(12) United States Patent
Heald

(10) Patent No.: US 8,708,975 B2
(45) Date of Patent: Apr. 29, 2014

(54) SYRINGE, AUTO-INJECTOR DEVICE AND SET OF AUTO-INJECTOR DEVICES AND SYRINGES

(75) Inventor: Michael Heald, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/202,441

(22) PCT Filed: Mar. 4, 2010

(86) PCT No.: PCT/EP2010/052791
§ 371 (c)(1),
(2), (4) Date: Jan. 6, 2012

(87) PCT Pub. No.: WO2010/100246
PCT Pub. Date: Sep. 10, 2010

(65) Prior Publication Data
US 2012/0101446 A1    Apr. 26, 2012

(30) Foreign Application Priority Data
Mar. 6, 2009  (EP) .................................... 09003281

(51) Int. Cl.
*A61M 5/00* (2006.01)
*A61M 5/31* (2006.01)

(52) U.S. Cl.
USPC ............................ 604/240; 604/241; 604/187

(58) Field of Classification Search
USPC ........................... 604/240–241, 110, 186, 187
See application file for complete search history.

(56) References Cited

U.S. PATENT DOCUMENTS

| 5,336,200 | A | 8/1994 | Streck et al. |
| 6,099,503 | A | 8/2000 | Stradella |
| 8,317,099 | B2 * | 11/2012 | Perkins et al. ................ 235/385 |
| 2007/0197978 | A1 | 8/2007 | Wortham |
| 2008/0132838 | A1 | 6/2008 | Wyrick |
| 2010/0042054 | A1 * | 2/2010 | Elahi et al. .................... 604/211 |

FOREIGN PATENT DOCUMENTS

| EP | 1486219 | 12/2004 |
| EP | 1902747 | 3/2008 |
| EP | 1912131 | 4/2008 |
| EP | 1932558 | 6/2008 |
| WO | 2005/080002 | 9/2005 |
| WO | 2008/107670 | 9/2008 |
| WO | 2009/003234 | 1/2009 |

OTHER PUBLICATIONS

European Search Report for EP Application No. 09003281, dated Aug. 17, 2009.
International Search Report and Written Opinion for Int. App. No. PCT/EP2010/052791, mailed Apr. 16, 2010.

* cited by examiner

*Primary Examiner* — Jason Flick
*Assistant Examiner* — Rebecca E Eisenberg
(74) *Attorney, Agent, or Firm* — McDonnell Boehnen Hulbert & Berghoff LLP

(57) ABSTRACT

A syringe comprising a first coding feature for mechanical interaction with a second coding feature of an auto-injector device is provided. The first coding feature is designed such that the syringe is only mountable in an auto-injector device having a second coding feature mating the first coding feature. Furthermore, an auto-injector device having a housing, wherein a syringe can be mounted, and a set of at least two auto-injector devices and syringes are provided.

14 Claims, 9 Drawing Sheets

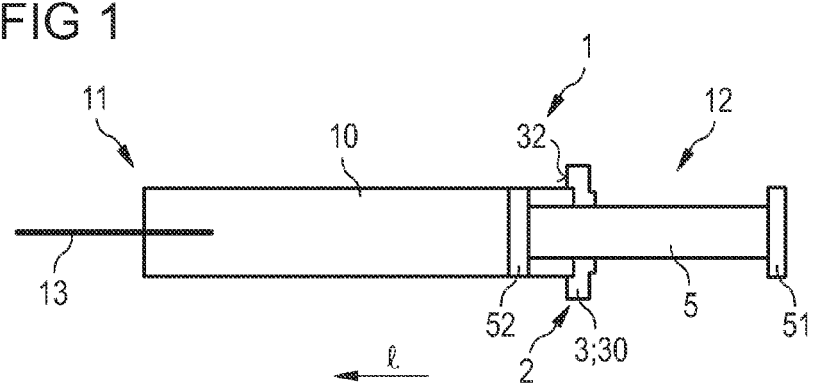
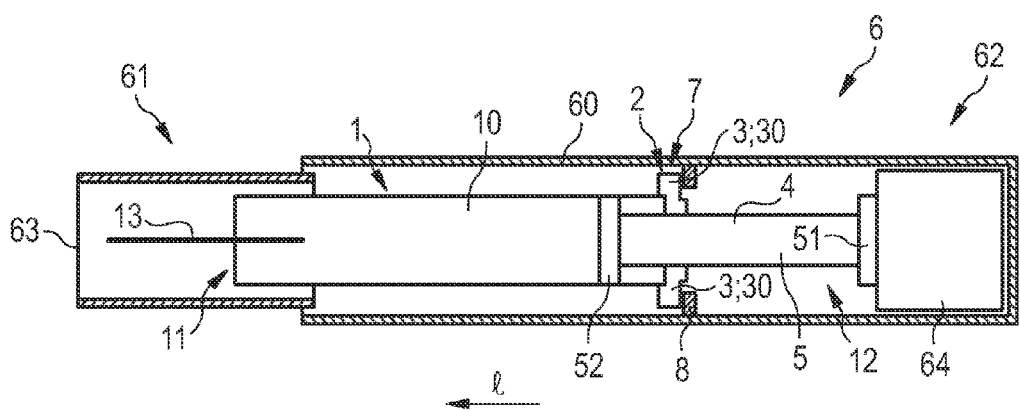

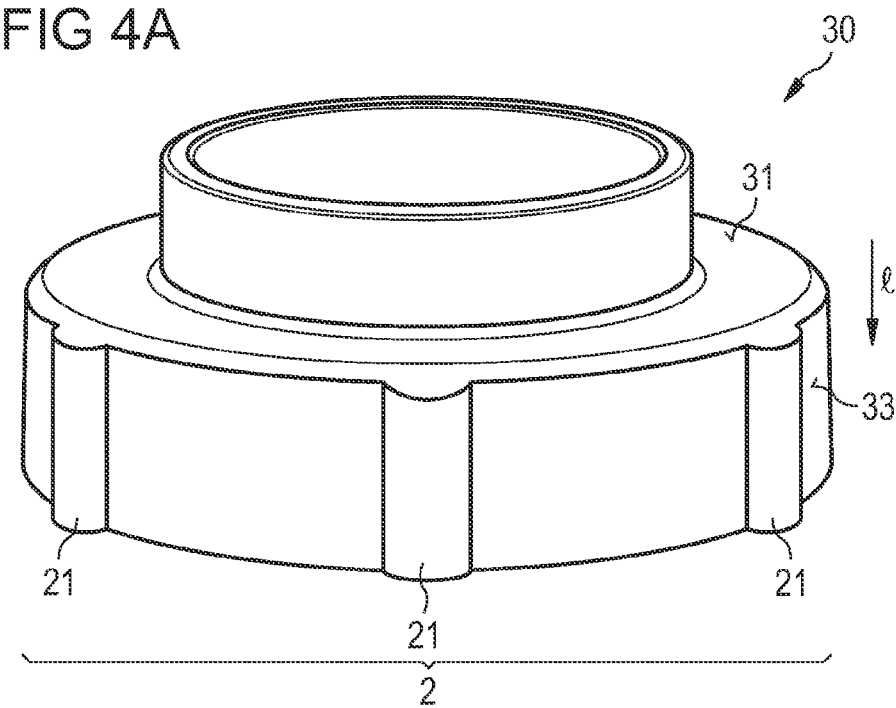
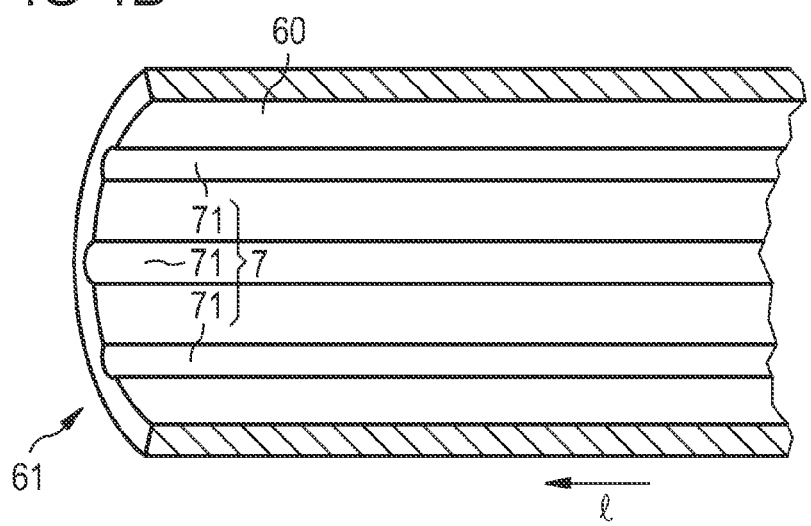

FIG 6A
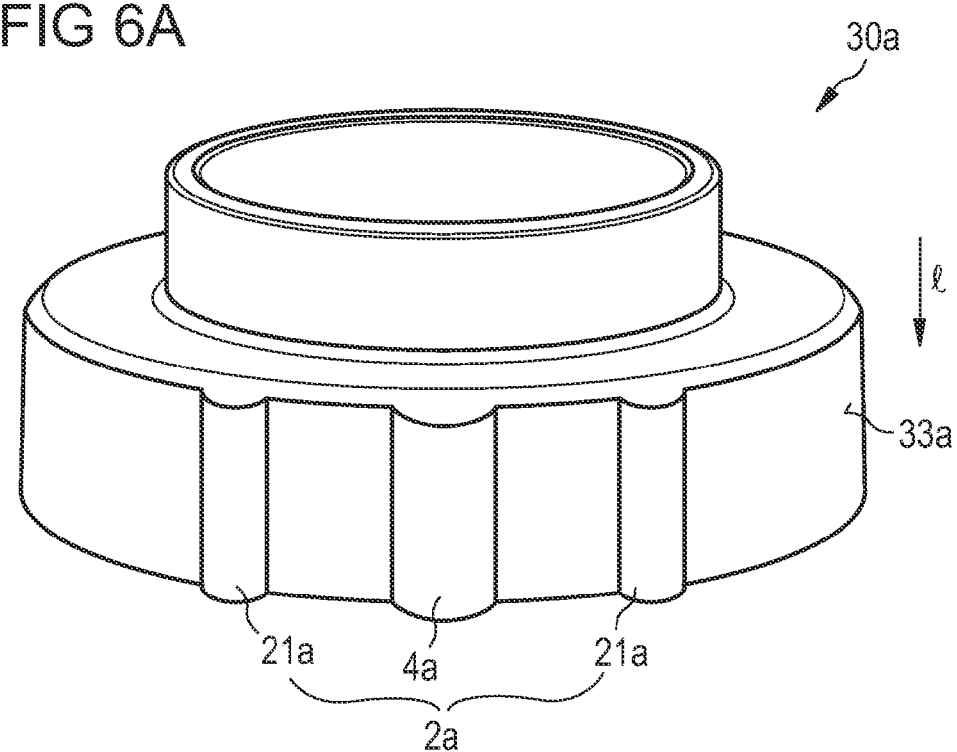
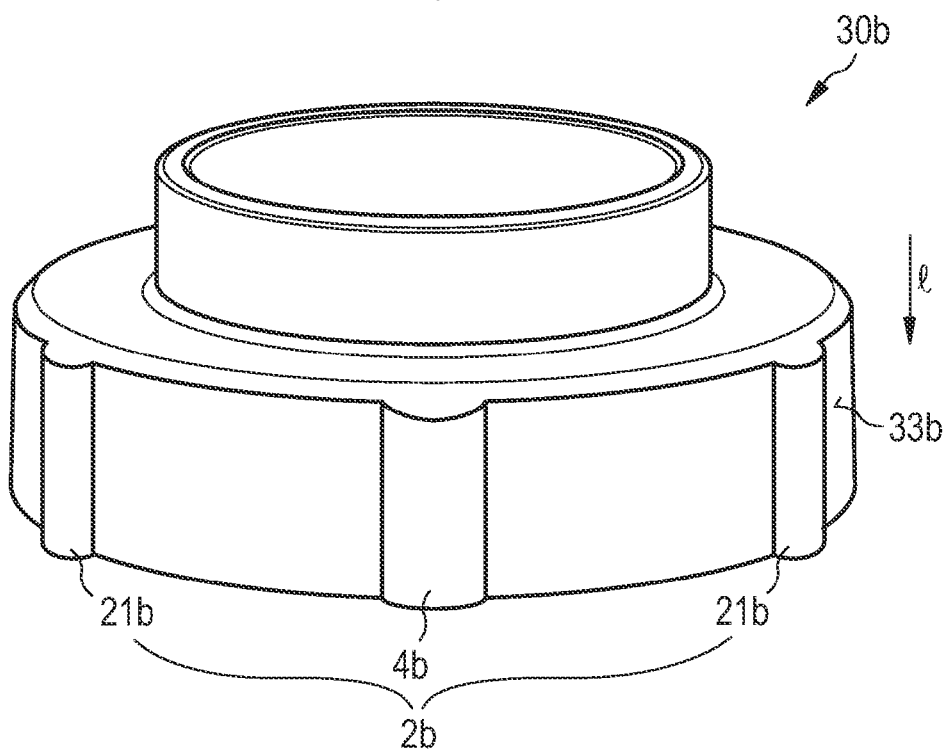

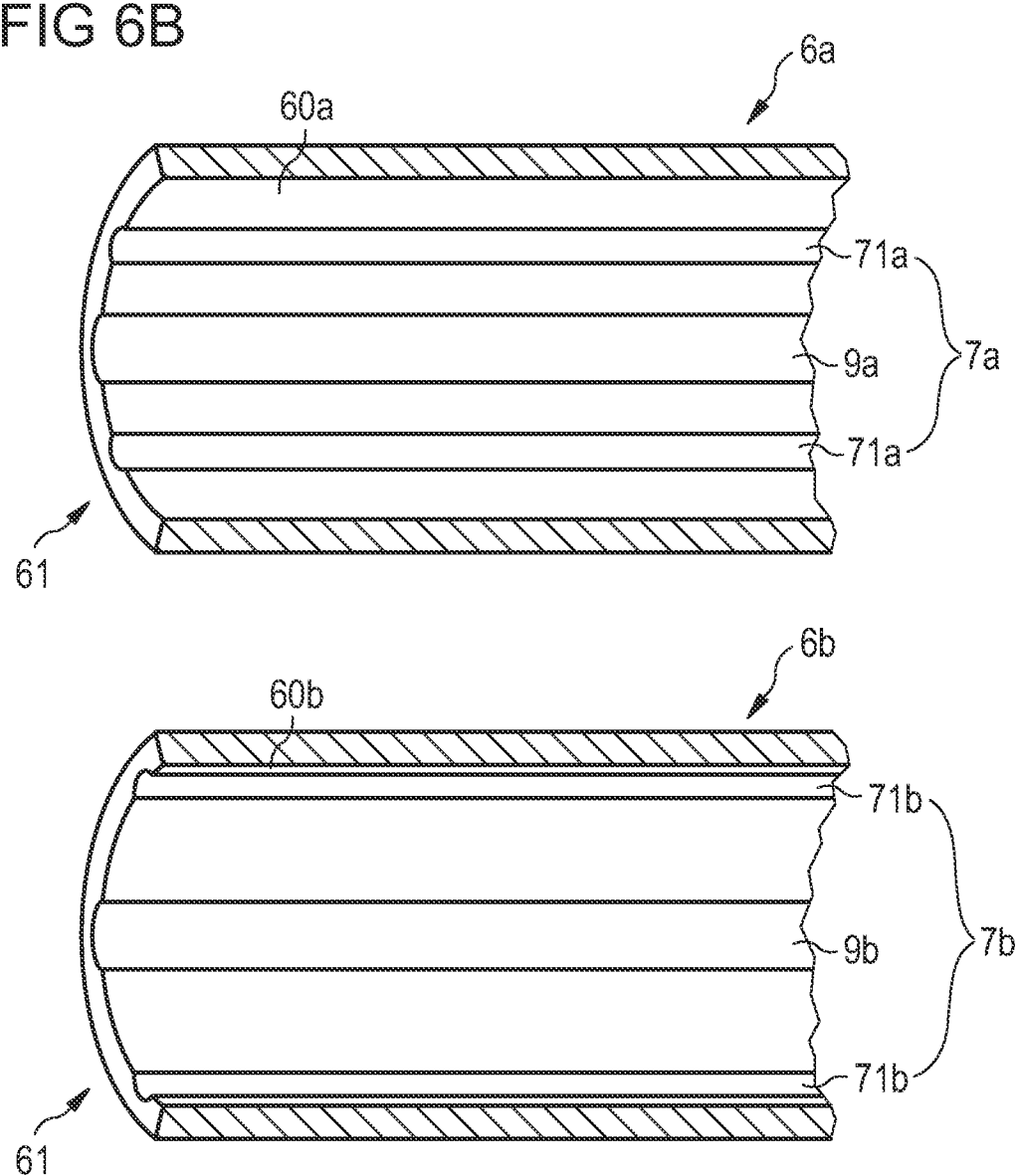

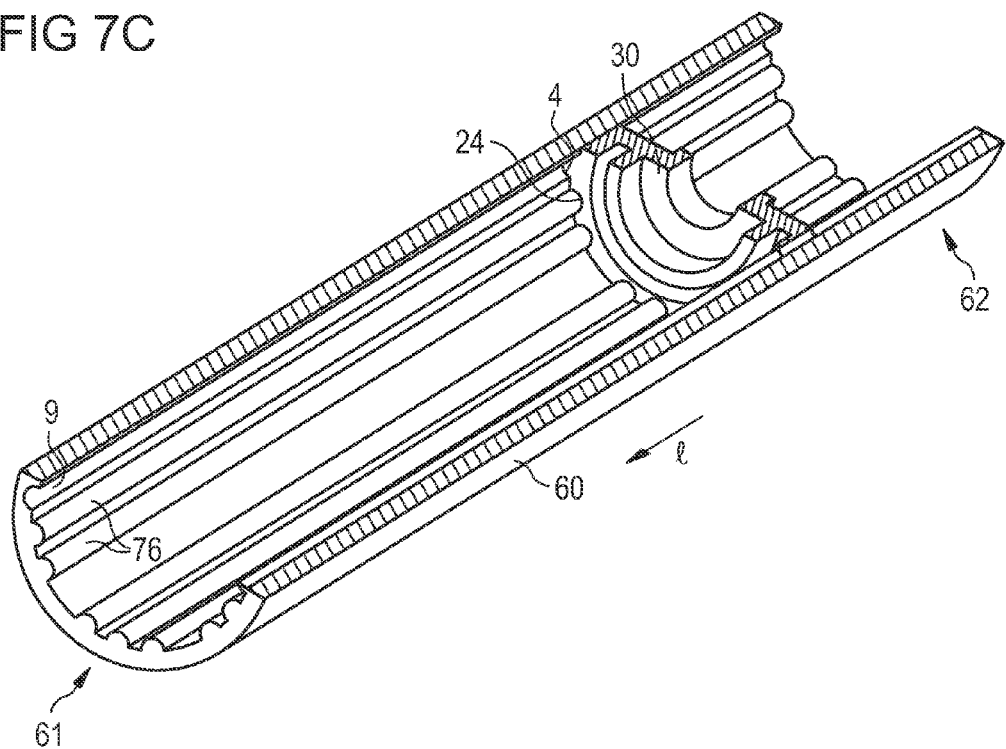
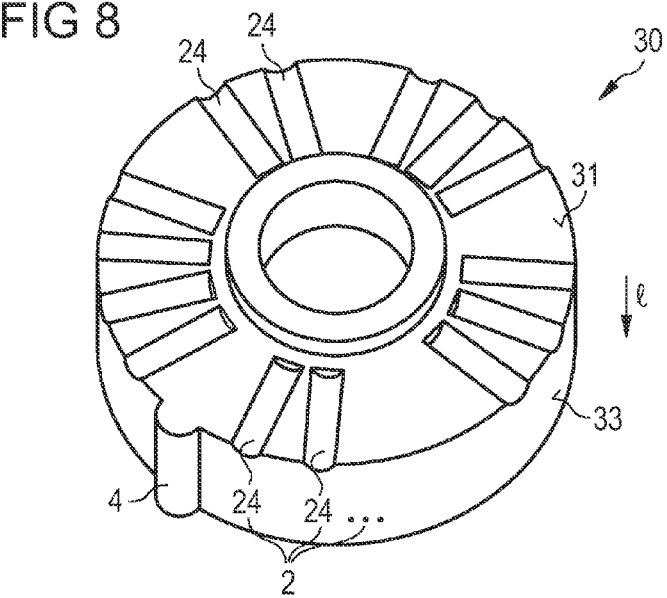

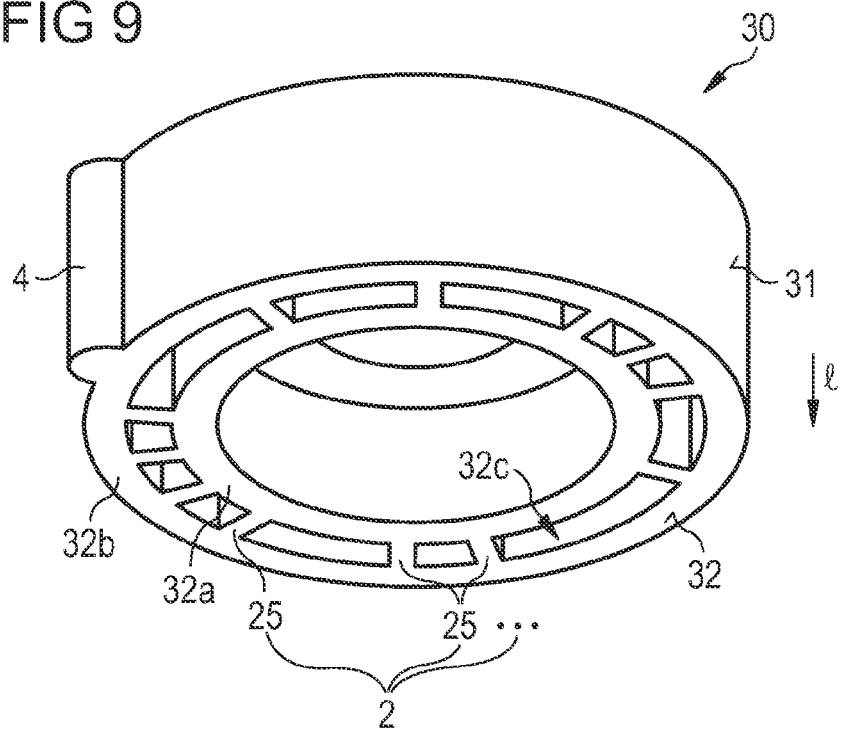
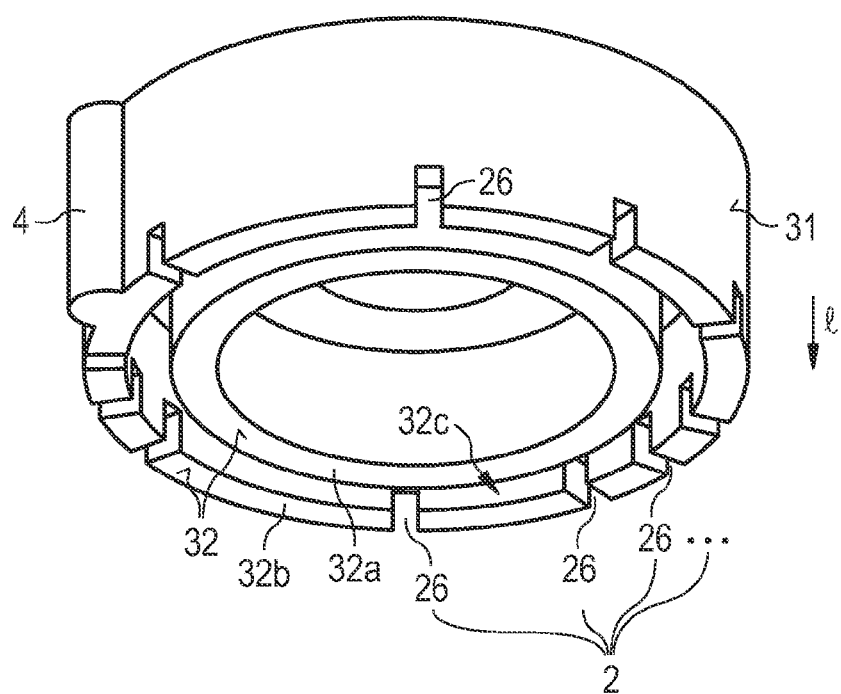

SYRINGE, AUTO-INJECTOR DEVICE AND SET OF AUTO-INJECTOR DEVICES AND SYRINGES

CROSS REFERENCE TO RELATED APPLICATIONS

The present application is a U.S. National Phase Application pursuant to 35 U.S.C. §371 of International Application No. PCT/EP2010/052791 filed Mar. 4, 2010, which claims priority to EP Patent Application No. 09003281.4 filed on Mar. 6, 2009. The entire disclosure contents of these applications are herewith incorporated by reference into the present application.

FIELD OF INVENTION

Auto-injector devices may be particularly useful for patients who are not familiar with the manual use of syringes or who have an aversion to penetrating their skin with a needle. By using an auto-injector device such problems can be circumvented. Here, the user is not required to supply the force for driving the needle into the skin and for dispensing the medicament. In many auto-injector devices, a user might not even have to see the needle.

This disclosure relates to syringes which can be mounted in auto-injector devices and to reloadable auto-injector devices, which can be loaded by mounting a syringe prefilled with a medicament. After the medicament has been dispensed, the syringe can be removed and the auto-injector device can be loaded with a new syringe.

BACKGROUND

The patent application EP 1932558 A1 and the publication WO 2008/107670 A2 disclose auto-injector devices. The patent application US 2008/0132838 A1 and the U.S. Pat. No. 6,099,503 disclose reloadable auto-injector devices.

The publication WO 2009/003234 A1 discloses a prefilled syringe having a retractable needle.

SUMMARY

It is an object of the invention to provide a syringe which can be mounted in an auto-injector device, wherein the risk for inserting a wrong syringe into an auto-injector device is minimised.

According to a first aspect of this disclosure, a syringe comprising a first coding feature for mechanical interaction with a second coding feature of an auto-injector device is provided. The first coding feature is designed such that the syringe is mountable in an auto-injector device having a second coding feature only if the first and second coding features match.

When the first and second coding features match, the mechanical interactions between the first and second coding features permit the full mounting of the syringe into the auto-injector device. The kind of mechanical interaction between the first and second coding feature depends on the specific designs of the coding features. As an example, when inserting the syringe in the auto-injector device, the first coding feature may positively fit into the second coding feature. In other embodiments, the first coding feature may fit into the second coding feature, wherein a gap is present between the first and second coding feature.

In a preferred embodiment, the syringe comprises a barrel containing a medicament. Preferably, the syringe is pre-filled with the medicament when it is handed over to the user. Thereby, the syringe is very simple to use, as the user is not required to draw the medicament into the syringe.

The barrel may comprise a distal end, where a needle is located, and a proximal end, where a plunger is partially inserted into the barrel. A medicament can be dispensed by moving the plunger toward the distal end of the syringe, whereby the medicament is pressed out of the barrel.

Preferably, the disclosed syringe can not only be used with an auto-injector device but can also be operated manually. Here, a user penetrates his or her skin with the needle and moves the plunger by depressing a button at the end of the plunger towards the distal end of the syringe. Preferably, the user places his or her thumb on the plunger button and exerts a force. In order to have a counter bearing for the exerted force and to give the user good control of the dispensing procedure, the syringe may have a finger flange. The finger flange may be a collar-like projection at the syringe, where the user can for example place his or her index and middle finger and thereby exert a counterforce. Such a finger flange may be located at the proximal end of the syringe barrel.

In a preferred embodiment, the first coding feature on the syringe is located such that it does not interfere with a manual operation of the syringe. Thereby, the disclosed syringe can be used both for manual operation and for operation with an auto-injector device. Accordingly, the manufacturing costs can be kept very low as only one type of syringe has to be produced.

In one embodiment, the first coding feature is fixed relative to the barrel containing a medicament.

Preferably, the barrel is made of a rigid material, for example glass or plastic. In this case, by a rigid first coding feature fixed to the barrel, a very robust and thus reliable coding may be achieved. Due to the rigidness of the barrel and the coding feature, the syringe may not be forced into a non-mating auto-injector device by an elastic deformation of the barrel or coding feature.

The first coding feature may be an integral part of the barrel.

In a preferred embodiment, the first coding feature is located on an element attached to the barrel.

The element may be moulded from a plastic material and may, for example, be glued to the barrel. In moulded plastic elements, first coding features can be very easily introduced and thus a cheap way of coding can be achieved.

In a preferred embodiment, the element attached to the barrel does already fulfil a certain function or is present due to the manufacturing process in a manually operated syringe. In this case, no additional element has to be attached to the syringe.

Such an element may be a finger flange located near the proximal end of the barrel. The first coding feature may be located at any other position of the barrel, for example at the distal end of the barrel. In particular, the first coding feature may be located at an element, which helps to fix the syringe in an auto-injector device. The first coding feature may also extend along the longitudinal axis of the syringe.

The first coding feature may comprise several coding portions located at different positions at the syringe. Here, the coding may be achieved by the cooperation of all coding portions.

Preferably, the first coding feature is located and designed such that the user is not distracted or even hindered when operating the syringe manually.

Preferably, the coding feature offers a number of possible coding permutations to provide individual codes for a plurality of drug products.

In a first embodiment, the first coding feature may be simply provided by the outer dimension of an element attached to the barrel or an element being an integral part of the barrel. Here, for example, the outer diameter of a collar-like finger flange attached to the barrel may serve as the first coding feature. By providing a plurality of finger flanges, each having a different diameter, a plurality of drugs can be encoded.

In a preferred embodiment, the first coding feature comprises at least one attribute selected from the group of a rib, a pin, a projection, a groove, an indent, a castellation, a stepped diameter and an angled plane. The attribute may be an integral part of the syringe or may be located at an element attached to the syringe. The first coding feature may comprise several attributes, for example a plurality of ribs, or a mixture of attributes, for example a plurality of ribs and a pin.

The second coding feature of the auto-injector device is designed such that it matches the first coding feature when the syringe is mountable in the auto-injector device. As an example, if the first coding feature comprises a plurality of ribs located at specific positions at the syringe, the second coding feature comprises a plurality of grooves at corresponding positions at the auto-injector device.

In one embodiment, the syringe has a longitudinal axis, wherein the first coding feature comprises a plurality of ribs extending towards the longitudinal axis. This may be particularly useful, when the syringe is inserted into the auto-injector device from the front or rear end of the auto-injector and along the longitudinal axis of the syringe. Here, first and second coding features extending along the longitudinal axis do not interfere with the insertion of the syringe into the auto-injector device.

In other embodiments, the syringe may be inserted into the auto-injector device from the top or bottom side of the auto-injector device along a direction perpendicular to the longitudinal axis. In such embodiments, first coding features comprising ribs extending perpendicular to the longitudinal axis may be useful.

In one embodiment, the syringe comprises an orientation feature which defines the orientation of the syringe during mounting the syringe into the auto-injector device.

Preferably, the orientation feature is designed such that the user is guided to insert the syringe in the correct orientation in the auto-injector device. Thus, the user does not have to twist the syringe and try several orientations until he or she recognises if the syringe is mountable or not mountable into a certain auto-injector device. The orientation feature may also have the double function of orientation and coding. The orientation feature may be part of or identical with the first coding feature.

According to a second aspect of the disclosure, an auto-injector device comprises a housing, wherein the disclosed syringe can be mounted, and a second coding feature for mechanical interaction with the first coding feature of the syringe.

The auto-injector device comprises an injection mechanism such that the user does not have to supply the force for injecting a medicament. Here, all possible embodiments of auto-injector devices may be used. As an example, the syringe may be mounted from a front side or a top side of the auto-injector device. The auto-injector device has activating means effecting the penetration of the needle into the skin and the dispensing of the medicament. Such activating means may be a spring, which moves the plunger towards the distal end of the syringe. The activating means may be triggered, for example, by depressing a button at the rear end of the auto-injector device or by pressing the front end of the auto-injector device onto the skin.

In a preferred embodiment, the second coding feature is defined such that only a syringe having a matching first coding feature can be fully assembled with the auto-injector device.

In the case that the second coding feature does not match the first coding feature, the syringe may be prevented from being fixed in the auto-injector device. In other embodiments, the non-matching second coding feature may prevent the housing of the auto-injector device from being closed after a wrong syringe has been inserted in the auto-injector device.

The second coding features may be located at a syringe fixation element.

Such an element may be a protrusion, for example a detent, at the inner part of the housing. Here, by the mechanical interaction of a second coding feature and a non-matching first coding feature the partial or full insertion into the housing may not be prevented. However, the mechanical interaction prevents the fixation of the syringe in the housing. Instead of preventing insertion or fixation of the syringe, the auto-injector device may lock-out and refuse to function, or may display a message to tell the user that a wrong syringe has been inserted.

In a further embodiment, the second coding feature may be designed such that only a syringe having a first coding feature matching the second coding feature can be inserted into the housing.

Here, the mechanical interaction of the first and the non-mating second coding feature may prevent the syringe from being even partially inserted into the housing.

The second coding feature may be located near the front end of the housing.

In this case, for an auto-injector device which can be loaded from the front end with a prefilled syringe, a partial insertion of the syringe can be prevented. In other embodiments, for example when the auto-injector device is loaded from the rear end of the housing, the second coding feature may be located at the rear end of the housing.

Preferably, the auto-injector device is designed such that the syringe is exchangeable.

Such reloadable auto-injector devices can be used several times and do not have to be disposed after only a single usage. This can be particularly useful for high quality and expensive auto-injector devices.

In a further aspect, a set of at least two auto-injector devices and at least two syringes is provided, wherein for each syringe the first coding feature is designed such that due to the mechanical interaction with the respective second coding feature of an auto-injector device each syringe is mountable in only one of the auto-injector devices.

Thereby, a user requiring several medicaments each dispensed by a specific auto-injector device is guided to mount the syringe containing a specific medicament into the correct auto-injector device. Each auto-injector device may be dedicated to dispensing a certain medicament or drug strength, and may be coded accordingly. As an example, the medicament name or a colour encoding a specific medicament is visible at the auto-injector device.

Preferably, for each syringe the first coding feature encodes the specific medicament contained in the syringe.

As an example, a manufacturer may produce syringes which may be filled with a medicament chosen from a plurality of medicaments. Accordingly, each syringe may comprise a first coding feature which is dedicated to the particular medicament and is chosen from a plurality of first coding features.

In another embodiment the drug delivery device comprises a medicament. The medicament could be pre-filled in a cartridge or, if the drug delivery device is designed as a syringe, pre-filled in the syringe.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Other features will become apparent from the following detailed description when considered in conjunction with the following drawings:

FIG. 1 is a schematic cross-sectional view of a syringe.

FIG. 2 is a schematic cross-sectional view of an auto-injector device with a syringe mounted therein.

FIG. 4A is a perspective view of a first embodiment of a first coding feature located at a finger flange.

FIG. 4B is a view of a second coding feature located at the inner part of the housing of an auto-injector device, which matches the first coding feature according to FIG. 4A.

FIG. 6A is a perspective view of a set of finger flanges having first coding features.

FIG. 6B is a view of the inner parts of the housings of auto-injector devices having second coding features matching the first coding features according to FIG. 6A.

FIG. 7C is a view of the finger flange according to FIG. 7a inserted in the housing of an auto-injector device according to FIG. 7B.

FIG. 8 is a perspective view of a further embodiment of a first coding feature located at a finger flange.

FIG. 9 is a perspective view of a further embodiment of a first coding feature located at a finger flange.

FIG. 10 is a perspective view of a further embodiment of a first coding feature located at a finger flange.

DETAILED DESCRIPTION

Figure 3A:
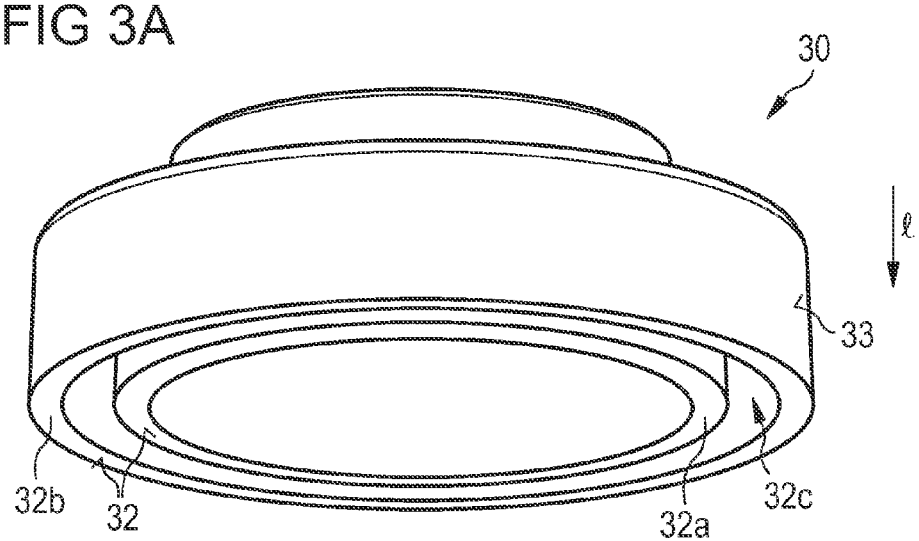
FIGS. 3A and 3B are perspective views of a finger flange.

In FIG. 1, a syringe 1 pre-filled with a liquid medicament, for example heparin, is shown. The syringe 1 comprises a barrel 10, wherein the medicament is retained. The barrel 10 is a glass barrel having a longitudinal axis 1 extending from the proximal end 12 to the distal end 11 of the syringe 1. At its distal end 11, the syringe 1 comprises a needle 4. At its proximal end 12, the syringe 1 comprises a plunger 5, which is partially inserted in the barrel 10. The plunger 5 is fixed to a plunger seal 52 arranged inside the barrel 10.

In a manual operation of the syringe 1, the plunger 5 is moved towards the distal end 11 of the syringe by depressing the button 51, for example with the thumb. Thereby, the plunger seal 52 moves towards the distal end 11 of the barrel 10, whereby the medicament is pressed out of the barrel 10. A finger flange 30 is attached to the barrel, whereby a counter bearing for the force exerted by the user on the plunger 5 is provided. When depressing the button 51 with his thumb, the user can place his index and his middle finger at the bottom face 32 of the finger flange 30 such that the barrel 10 is located between these fingers and exert a counterforce.

The finger flange 30 is an element 3 which is attached to the barrel 10. It may be a moulded plastic element glued or clipped to the barrel 10. Such an element 3 may also have further functions, for example the functions of a release ring triggering the retraction of the needle after the medicament has been dispensed as described in document WO 2009/003234 A1. The syringe comprises a first coding feature 2, which is located at the finger flange 30.

FIG. 2 shows an auto-injector device 6, wherein a syringe 1 as shown in FIG. 1 is mounted. The auto-injector device 6 comprises a housing 60 wherein the syringe 1 is retained. The syringe 1 is fixed by fixation elements 8 in the auto-injector device 6. When a user wants to dispense a dose, he presses the auto-injector device 6 onto his skin and optionally depresses a button (not shown here), whereby activation means 64 are triggered. By the activation means 64, the needle 4 is moved forward and pierces a membrane 63 at the front end 61 of the auto-injector device 6. Furthermore, by the activation means 64 the plunger 5 is moved towards the distal end 11 of the syringe 1, whereby the medicament is pressed out of the barrel 10. For clarity reasons, further details of the activation means 64 and the fixation means 8 are not shown here.

The auto-injector device 6 comprises a second coding feature 7, which is located near the fixation means 8. Thereby, the syringe 1 can only be fixed in the auto-injector device 6, if the second coding feature 7 matches the first coding feature 2. In the case that the second coding feature 7 does not match the first coding feature 2, the full assembly of the syringe 1 and the auto-injector device 6 will be prevented.

The type of coding is not restricted to the syringes and auto-injector devices as shown here. As an example, the syringe may have a dual chamber. Moreover, the syringe needle may be capped and a de-capping device may be built into the auto-injector device. This may be particularly useful in a re-usable auto-injector.

Figure 3B:
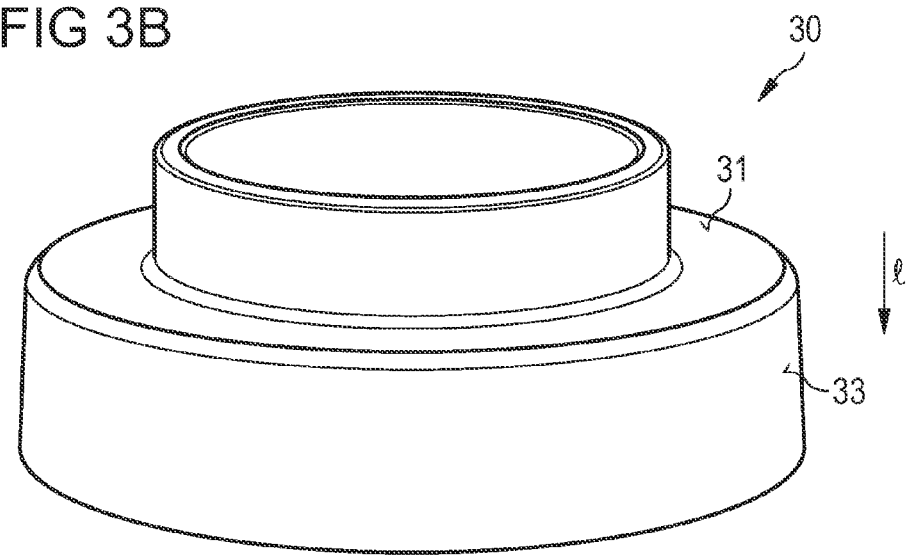

FIGS. 3A and 3B show perspective views of the finger flange 30 attached to the proximal end 12 of the syringe 1 as shown in FIGS. 1 and 2. Here, faces suitable for a first coding feature 2 are identified. In the case that the finger flange 30 also serves as a release ring as shown in document WO 2009/003234 A1 several outer faces of the finger flange 30 may be covered by parts of the plunger 5 and thus are not always accessible from the outside. The finger flange 30 comprises an inner cylindrical section 32a and an outer cylindrical section 32b, which are concentrically arranged. The inner cylindrical section 32a has a smaller diameter than the outer cylindrical section 32b and a space 32c is accessible from the bottom face 32 of the finger flange 30 between the inner 32a and outer 32b cylindrical section.

Preferably, the first coding feature 2 is located at a part of the finger flange 30 which is always accessible from the outside and which does not hinder or distract a user when operating the syringe 1 manually. Such suitable faces are, for example, the side face 33 facing away from the longitudinal axis 1 of the syringe. Furthermore, also parts of the top face 31 of the finger flange 30 may be suitable for a first coding feature 2. In addition to that, the first coding feature 2 may be located in the space 32c between the inner 32a and the outer 32b cylindrical section. Such a first coding feature 2 may be a plastic web, of variable width and height, extending from the inner 32a to the outer 32b cylindrical section. Instead of or in addition to that attributes of a first coding feature 2, for example protrusions or indents, may be located at the bottom face 32 of the finger flange 30.

FIG. 4A shows a finger flange 30 having a first coding feature 2 which comprises several ribs 21 located at the side face 33 of the finger flange 30. The ribs 21 extend along the longitudinal axis 1 of the barrel 10 and are arranged at a specific angular spacing around the longitudinal axis 1.

FIG. 4B shows the inside part of the housing 60 of an auto-injector device 6 having a second coding feature 7 mating the first coding feature as shown in FIG. 4A. The coding feature 7 comprises several grooves 71 which are arranged at positions corresponding to the positions of the first coding feature 2. The second coding feature 7 extends from the front end 61 of the housing 60 such that the syringe 1 can only be inserted into the housing 60 when the first coding feature 2 matches the second coding feature 7. Thereby, an insertion of a wrong syringe 1 is prevented.

In other embodiments, a number of ribs 21 and grooves 71 at varying angular positions around the perimeters of the finger flange 30 and the housing 60 are provided. Thereby, the number of available coding permutations can be significantly increased.

Figure 5A:
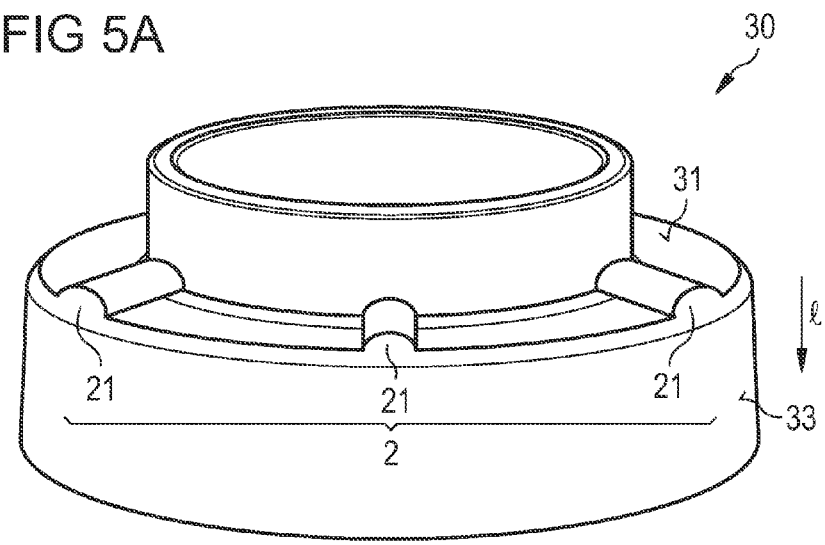
FIG. 5A is a perspective view of a second embodiment of a first coding feature located at a finger flange.

FIG. 5A shows a second embodiment of a finger flange 30 having a first coding feature 2 comprising ribs 21 located at the top face 31 of the finger flange 30.

Figure 5B:
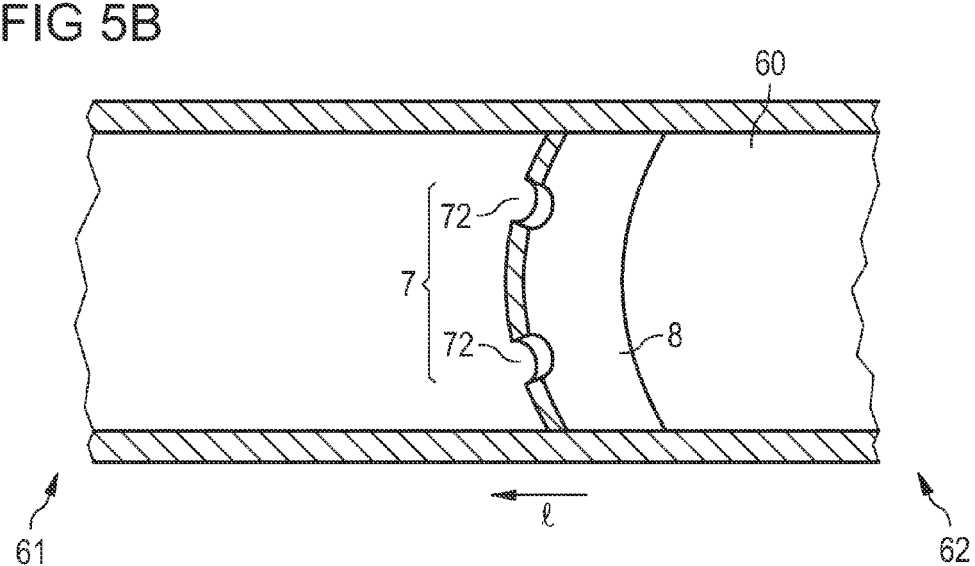
FIG. 5B is a view of a second coding feature located at the inner part of the housing of an auto-injector device, which matches the first coding feature according to FIG. 5A.

FIG. 5B shows the inner part of a housing 60 having a mating second coding feature 7 comprising slits 72 located at a syringe fixation element 8. By such a second coding feature 7, a full assembly of a syringe 1 having a non-mating first coding feature 2 can be prevented, while a partial insertion of such a syringe 1 in the auto-injector device 6 is allowed.

FIG. 6A shows a set of finger flanges 30a, 30b each comprising a first coding feature 2a, 2b. Each first coding feature 2a, 2b comprises ribs 21a, 21b located at the side faces 33a, 33b of the finger flanges 30a, 30b. The arrangements of the ribs 21a, 21b differs between the finger flanges 30a, 30b, whereby the coding function of the first coding features 2a, 2b is achieved. In the first finger flange 30a the angular spacing of the ribs 21a is less than for the ribs 21b of the second finger flange 30b. Furthermore, each finger flange 30a, 30b comprises a first orientation feature 4a, 4b, whereby the user easily recognises the correct orientation of the syringe 1 relative to the auto-injector device 6 when inserting the syringe 1 in the auto-injector device 6. The first orientation features 4a, 4b are ribs having a larger cross section than the ribs 21a, 21b of the first coding features 2a, 2b.

FIG. 6B shows a set of second coding features 7a, 7b located at inner parts of the housings 60a, 60b of auto-injector devices 6a, 6b. Here, the second coding feature 7a of the first auto-injector device 6a comprises grooves 71a matching the first coding feature 2a of the first finger flange 30a shown in FIG. 6A. The second coding feature 7b of the second auto-injector device 6b comprises grooves 71b matching the first coding feature 2b of the second finger flange 30b shown in FIG. 6A. The housings 60a, 60b comprise second orientation features 9a, 9b which mate the first orientation features 4a, 4b shown in FIG. 6A.

When trying to insert a syringe 1 having one of the finger flanges 30a, 30b shown in FIG. 6A in one of the auto-injector devices 6a, 6b, a user will first align the first 4a, 4b and second orientation features 9a, 9b. Then, the user instantly recognises if a first coding feature 2a, 2b mates the second coding feature 9a, 9b and thus recognises if a syringe 1 is mountable in a certain auto-injector device 6a, 6b.

Figure 7A:
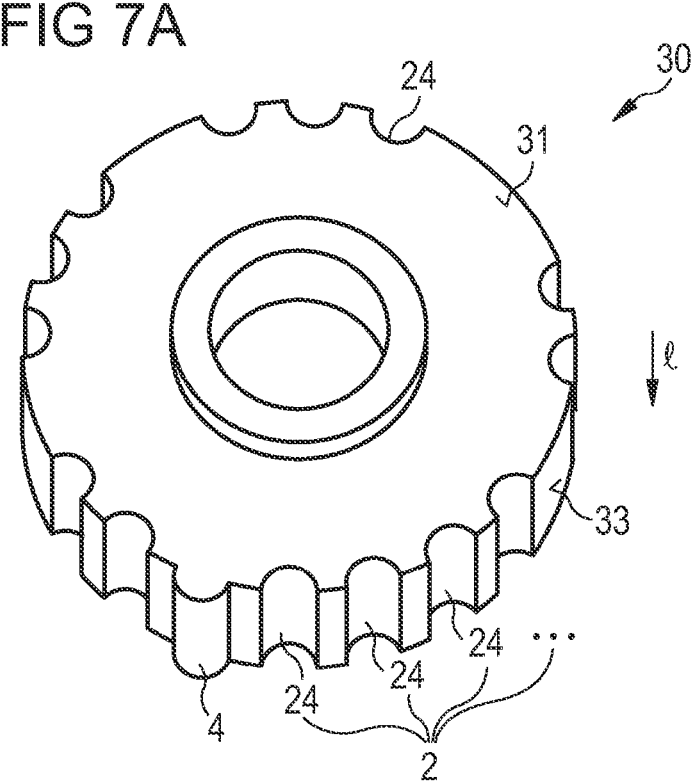
FIG. 7A is a perspective view of a further embodiment of a first coding feature located at a finger flange.

FIG. 7A shows a further embodiment of a finger flange 30 having a first coding feature 2 and a first orientation feature 4. The first coding feature 2 comprises grooves 24 located at the side face 33 of the finger flange 30. The coding function is provided by the number and the angular distribution of the grooves 24. Furthermore, at the side face 33 of the finger flange 30, a first orientation feature 4 in the form of a rib extending along the longitudinal axis 1 is located.

By varying the number and the angular distribution of the grooves 24, a plurality of finger flanges 30 each having a specific code for a specific drug product can be provided. By attaching the coded finger flange 30 to a syringe prefilled with the drug product, a coding of the syringe can be achieved.

Figure 7B:
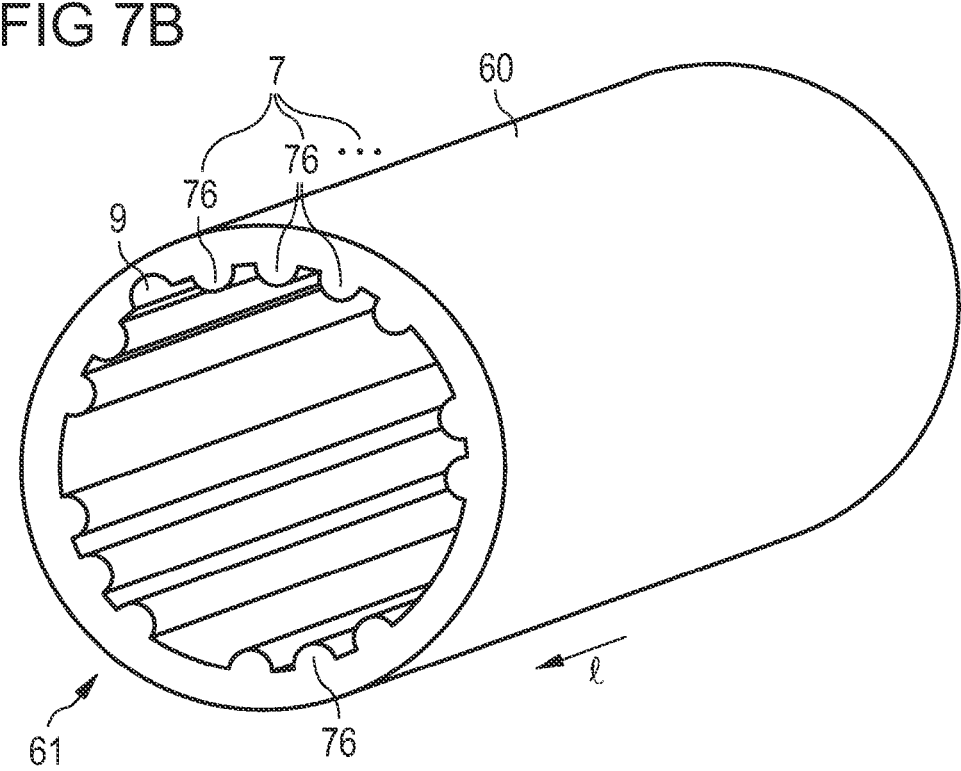
FIG. 7B is a view of a second coding feature located at the inner part of the housing of an auto-injector device, which matches the first coding feature according to FIG. 7A.

FIG. 7B shows a housing 60 of an auto-injector device 6 having a second coding feature 7, which matches the first coding feature 2 of the finger flange 30 according to FIG. 7A. The second coding feature 7 comprises a plurality of ribs 76 extending from the front end 61 of the inner part of the housing 60 towards its rear end 62. Furthermore, the housing 6 comprises a second orientation feature 9 which matches the first orientation feature 4 of the finger flange 30. The second orientation feature 9 has the form of a groove, wherein the rib of the first orientation feature 4 can be accommodated.

FIG. 7C shows the finger flange 30 according to FIG. 7A inserted in the housing of the auto-injector device according to FIG. 7B. The finger flange 30 is attached to the proximal end 12 of a syringe barrel 10. For reasons of clarity, the syringe 1 is not shown here.

FIG. 8 shows a further embodiment of a finger flange 30 having a first coding feature 2 and a first orientation feature 4. The first coding feature 2 comprises several grooves 24 located at the top face 31 of the finger flange 30. The coding function is provided by the number and the angular distribution of the grooves 24. Furthermore, at the side face 33 of the finger flange 30, a first orientation feature 4 in the form of a rib extending along the longitudinal axis 1 is located.

Preferably, a plurality of finger flanges 30 differing in the angular distribution or number of grooves 24 is provided, whereby each first coding feature 2 encodes a specific drug product.

FIG. 9 shows a further embodiment of a finger flange 30 having a first coding feature 2 and a first orientation feature 4. The first coding feature 2 comprises several bars 25 located in the space 32c between the inner 32a and the outer 32b cylindrical section. The bars 25 extend from the inner cylindrical section 32a towards the outer cylindrical section 32b. The coding function is provided by the number and the angular distribution of the bars 25. Furthermore, at the side face 33 of the finger flange 30, a first orientation feature 4 in the form of a rib extending along the longitudinal axis 1 is located.

Preferably, a plurality of finger flanges 30 differing in the angular distribution or number of bars 25 is provided, whereby each first coding feature 2 encodes a specific drug product. Similarly, a plurality of auto-injector devices 6 having second coding features 7 is provided, whereby each second coding feature 7 encodes a specific drug product. By attaching the finger flanges 30 to syringes 1 containing a specific drug product, a mapping between the syringes 1 and the auto-injector devices 6 can be achieved, such that a syringe 1 is mountable in an auto-injector device 6 only if the first 2 and second coding features 7 match.

FIG. 10 shows a further embodiment of a finger flange 30 having a first coding feature 2 and a first orientation feature 4. The first coding feature 2 comprises several slits 26 located at the bottom side 32 of the outer cylindrical section 32b. The coding function is provided by the number and the angular distribution of the slits 26. Furthermore, at the side face 33 of the finger flange 30, a first orientation feature 4 in the form of a rib extending along the longitudinal axis 1 is located.

Preferably, a plurality of finger flanges 30 differing in the angular distribution or number of slits 26 is provided, whereby each first coding feature 2 encodes a specific drug product.

The invention claimed is:

1. A syringe comprising
a barrel having a distal portion, a proximal portion and an interior defined by side walls to directly hold a medicament, where the proximal portion of the barrel has a finger flange;
a needle fixed to the distal portion of the barrel;
a plunger seal slidably positioned within and in direct contact with the side walls of the barrel interior;
a plunger fixed to the plunger seal where a portion of the plunger extends proximally outside of the barrel interior;
a first coding feature located on the barrel for mechanical engagement with a second coding feature of an auto-injector device configured to effect penetration of the needle into skin and to then dispense the medicament, where the syringe is configured to operate manually as a stand alone injection device by engaging the finger flange and plunger with fingers on one hand and pushing the plunger distally after needle insertion into skin, and
wherein the first coding feature is designed such that the syringe is mountable in an auto-injector device having a second coding feature only if the first and second coding features match and where the first coding feature is configured such that the syringe may not be forced into a non-mating auto-injector.

2. The syringe according to claim 1, wherein the first coding feature is located at an element attached to the barrel.

3. The syringe according to claim 2, wherein the element is the finger flange.

4. The syringe according to claim 1, wherein the first coding feature comprises at least one attribute selected from the group of a rib, a bar, a pin, a projection, a groove, a slit, an indent, a castellation, a stepped diameter and an angled plane.

5. The syringe according to claim 1, having a longitudinal axis (I),
wherein the first coding feature comprises a plurality of ribs extending towards the longitudinal axis.

6. The syringe according to claim 5, wherein the syringe comprises a first orientation feature which defines the orientation of the syringe during mounting the syringe into the auto-injector device.

7. An auto-injector device comprising:
a housing, wherein a syringe according to claim 1 can be mounted and
a second coding feature for mechanical interaction with the first coding feature of the syringe.

8. The auto-injector device according to claim 7, wherein the second coding feature is designed such that only a syringe having a first coding feature mating the second coding feature can be fully assembled with the auto-injector device.

9. The auto-injector device according to claim 8, wherein the second coding feature is located near a syringe fixation element.

10. The auto-injector device according to claim 7, wherein the second coding feature is designed such that only a syringe having a first coding feature mating the second coding feature can be inserted into the housing.

11. The auto-injector device according to claim 10, wherein the second coding feature is located near the front end of the housing.

12. The auto-injector device according to claim 11, wherein the syringe is exchangeable.

13. A set of at least two auto-injector devices according to claim 7 and at least two syringes according to claim 1,
wherein for each syringe the first coding feature is designed such that due to the mechanical interaction with the respective second coding feature each syringe is mountable in only one of the auto-injector devices.

14. A set according to claim 13, wherein for each syringe the first coding feature encodes a specific medicament contained in the syringe.

* * * * *